Figure 1:
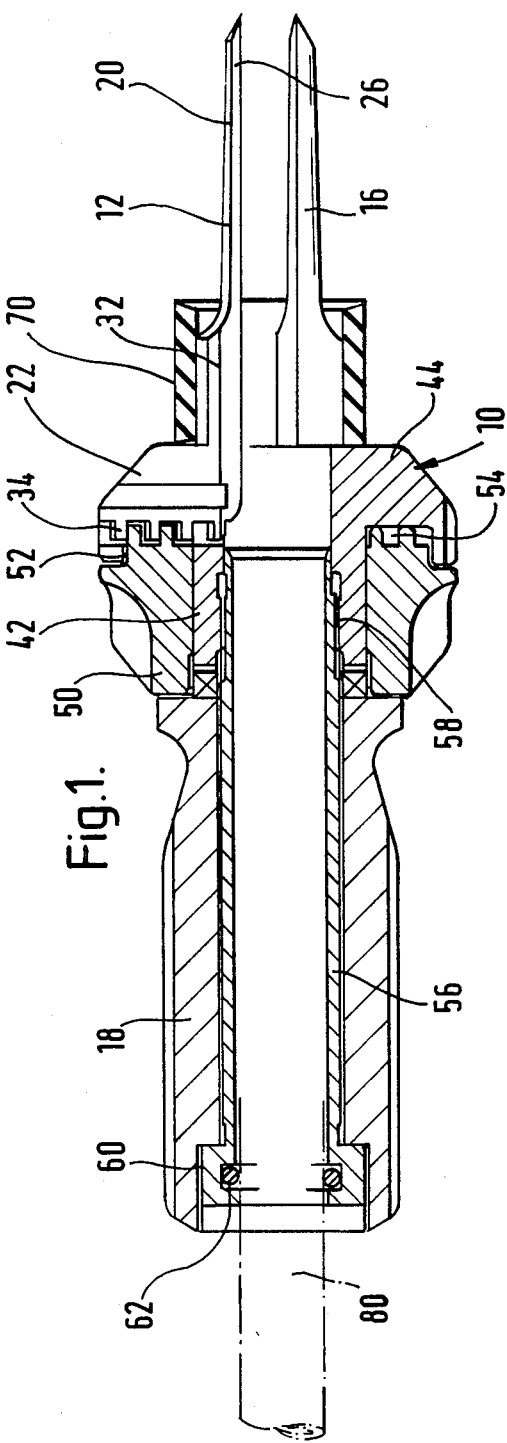

United States Patent [19]

Gill

[11] Patent Number: 4,617,929
[45] Date of Patent: Oct. 21, 1986

[54] SURGICAL APPLIANCE AND A METHOD FOR INTRODUCING DRAINAGE TUBING INTO CAVITIES

[76] Inventor: Steven S. Gill, 17A Hampstead Hill Gardens, Hampstead, London NW3, England

[21] Appl. No.: 621,521

[22] Filed: Jun. 18, 1984

[30] Foreign Application Priority Data

Jun. 18, 1983 [GB] United Kingdom ............... 8316640

[51] Int. Cl.$^4$ ............................................. A61F 17/32
[52] U.S. Cl. .................................................. 128/305.3
[58] Field of Search ......................... 128/305.3, 200.26; 604/272

[56] References Cited

U.S. PATENT DOCUMENTS

| | | | |
|---|---|---|---|
| 3,182,663 | 5/1965 | Abelson | 128/305.3 |
| 3,384,087 | 5/1968 | Brummelkamp | 128/305.3 |
| 3,643,649 | 2/1972 | Amato | 128/305.3 |
| 3,688,773 | 9/1972 | Weiss | 128/305.3 |
| 4,291,690 | 9/1981 | Jessen | 128/305.3 |

Primary Examiner—Robert Peshock
Assistant Examiner—Wenceslao J. Contreras
Attorney, Agent, or Firm—Thomas R. Vigil

[57] ABSTRACT

The surgical appliance is capable of being temporarily placed in a body for assisting in the passage of a tube through a puncture formed in the skin of the body. Contraction of the skin around the tube, once the appliance is removed, assists in holding the tube in place. The surgical appliance comprises a trochar having a proximal end and a distal end. The trochar is divided into a plurality of separate components. At least one tooth is provided on the proximal end of each of the components and a rotary actuator having a central channel therethrough is also provided for actuating the plurality of trochar components. A spiral formation on the actuator cooperates with the teeth on the trochar components so that rotation of the actuator about the longitudinal axis of the trochar produces parallel radial motion from each of the trochar components having at least one tooth thereon with respect to each other from a closed position in which such components lie substantially parallel and adjacent to each other thereby forming a composite trochar, to an open position wherein such components are substantially axially parallel with each other and separated radially to create a trochar central channel through the trochar components. The trochar central channel formed within the trochar components forms a continuation of the first named central channel through the actuator to provide a channel within the appliance through which a tube can be positioned with one end thereof extending into the puncture. The appliance is then removed from around the tube to leave only the tube in place within the puncture formed in the skin, with contraction of the skin adjacent the puncture around the tube, upon removal of the appliance, assisting in holding the tube in place.

7 Claims, 9 Drawing Figures

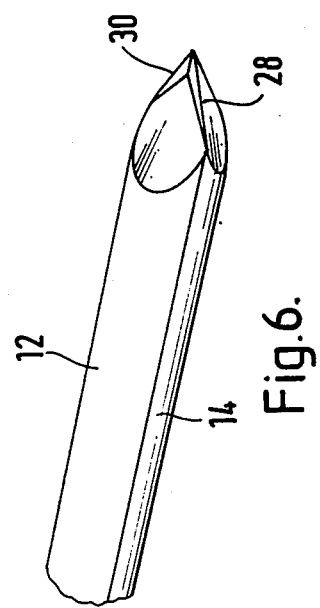
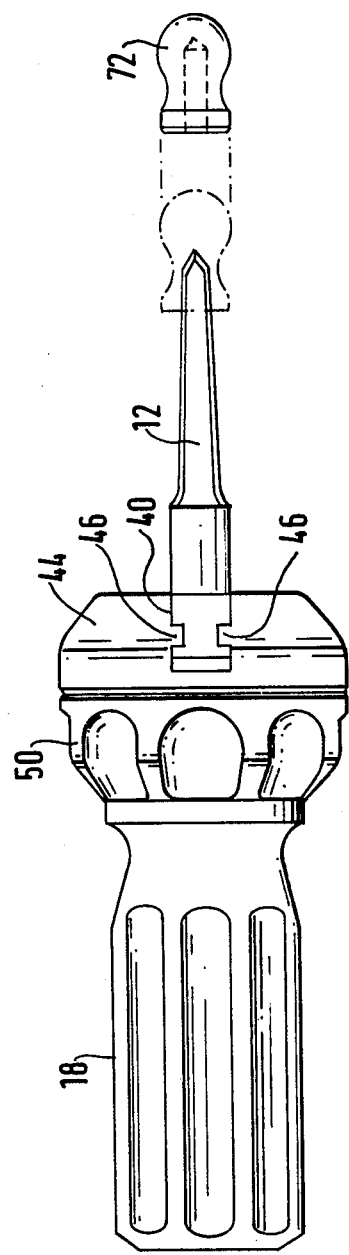

SURGICAL APPLIANCE AND A METHOD FOR INTRODUCING DRAINAGE TUBING INTO CAVITIES

The present invention relates to a surgical appliance and to a method for introducing drainage tubing, scopes, instruments or other surgical apparatus into cavities, and is concerned in particular, but not exclusively, with such an appliance for introducing drainage tubing into the thoracic cavity.

The indication for the insertion of all thoracic drains is to enable a collapsed or partially collapsed lung to be re-expanded thereby improving pulmonary function. The cause of the deflated lung may be from trapped intrathoracic air, from blood, pus, chyle, or oesophageal contents resulting from rupture of a mediastinal viscus.

The current method of thoracic drain insertion requires initially the cleaning of the skin at the site of insertion under sterile conditions. The commonly used sites are in the anterior axillary line through the fifth intercostal space; anteriorly in the mid-clavicular line; the second intercostal space, or posteriorly through the first intercostal space. Local anaesthetic is infiltrated into the intercostal space, traversing the upper border of a rib. A 2 centimeters long incision is made at the site, and two sutures are inserted, one for securing the drain in place, and a second, more loosely applied, purse string suture for use in subsequent closure of the incision when the drain is removed. Dissection is made through the connective tissue and intercostal muscle to the pleura. The chest drain can be inserted by means of an Argyle-type assembly, in which the drain is placed over a long trochar and forced through the incision into the pleural space, and the central trochar then removed. Alternatively, it can be introduced using the Tudor-Edwards assembly in which a trochar with surrounding cannula are pushed through the incision into the pleural space, the trochar withdrawn and the drainage tube is then passed through the cannula and the cannula removed over the drain leaving the drain alone in situ. Both the Argyle trochar, and the Tudor-Edwards trochar and cannula can be made to various sizes to accept standard catheters, such as 22F and 26F of sizes 8 millimeters and 9.5 millimeters in diameter respectively. Once the drain is in situ it is secured with a suture and connected to the underwater arm of an underwater seal drain.

When the lung is fully expanded, the drain is withdrawn and the purse string suture tightened to occlude the aperture.

The disadvantages of the available methods of thoracic drain insertion mentioned above are:

(i) Despite making a relatively large incision at the site of insertion, it is not possible to insert the drain and trochar, which is approximately 1 centimeter diameter, without exerting an appreciable force.

(ii) A large incision with adequate dissection and the insertion of the drain results in almost inevitable infection at the site of insertion and increased risk of haemorrhage.

(iii) A large incision may make chest drain insertion less hazardous as less force is required on insertion, but the chest drain will not function unless there is an airtight seal around its site of insertion in the chest wall. Further, unless the chest wall grips the drain tightly, it is likely to fall out or exert undue tension on the securing suture.

(iv) The major danger of inserting the Argyle chest drain and trochar is that: as the 1 centimeter diameter drain is forced through the intercostal muscles, there is a sudden yielding of the muscles as the trochar enters the chest cavity. Unless the forward motion is rapidly and expertly controlled, there is a great danger of perforating the lung, major vessels or the heart, all of which are recognised complications.

(v) It is necessary to have trochars of various sizes, because one size of trochar is only able to be used with a corresponding size of tube. In the case of the Argyle apparatus a separate trochar is required for each size of drain tube, and in the case of the Tudor-Edwards apparatus, a separate trochar and cannula is required for each size of drain.

(vi) On withdrawal of the chest drain, a channel up to 1 centimeter diameter may be left at the drain insertion site (this is between the chest cavity and the atmosphere). The equalisation of pressures can result in the re-collapse of the lung unless the purse string suture is pulled tight simultaneously with withdrawal of the chest drain to occlude the aperture. This is a difficult procedure especially if done single handedly.

(vii) Purse string sutures, when tightened around a line incision give very poor approximation of wound edges with increased risk of infection, poor haemostasis, poor wound healing and result in an ugly scar.

(viii) The whole procedure is time consuming, dangerous and frightening, and often painful to the patient.

By contrast, use of the present invention reduces or eliminates some or all of the problems outlined above. In particular, it is an object of the present invention to provide a surgical appliance which can be introduced into the thoracic cavity, without in some cases, prior incision or dissection, and without the danger of perforating major vessels or organs, and which can then be expanded to an appropriate diameter, stretching the tissues to allow the introduction of a drain, scope or other surgical instrument. When the appliance is withdrawn, leaving the drain, or instrument in situ, the stretched tissues contract, gripping it firmly, thereby reducing the chance of its displacement, the risk of haemorrhage or infection. When the drain or instrument is removed, the stretched tissues contract further to occlude the aperture, preventing air entering the pleural space and re-collapsing the lung, and leaving only a small puncture hole, not requiring a purse string suture.

According to this invention, a surgical appliance for the insertion of a tube through the skin comprises a trochar, divided into a plurality of separate components, and an actuator, to which the trochar components are connected so that they can be moved by operation of the actuator, radially with respect to each other from a closed position in which they lie substantially parallel and closely adjacent to each other, to an open position where they are substantially parallel but separated radially to create a central channel through the trochar components.

Preferably, the trochar has a sharp distal end. It is further preferred, that there is a central opening through the actuator which when the trochar components are opened is in continuation of the central channel through those components, whereby it is possible to pass a tube though the entire appliance when the trochar components are opened.

According to a preferred feature of the invention, the appliance is provided with an annular tube seal adapted to seal between the appliance and a tube passed through it, and an annular front seal adapted to seal between the appliance and the skin of the patient when the appliance is being used, the two seals together providing at least a restriction on the access of air to the site where the trochar penetrates the skin.

Preferably, the actuator is adapted to hold the trochar components in a parallel relationship with each other during the radial movement. In the preferred construction, the actuator includes a member rotatable about the longitudinal axis of the trochar, this member having a spiral formation co-operating with at least one tooth on each of the trochar components, so that rotation of the rotatable member produces parallel radial motion of the trochar components.

According to another preferred feature of the invention, the tooth or teeth on each trochar component is or are provided on a block extending radially from the proximal end of the component. Preferably each of the blocks is received in a radial slot in an actuator body, the rotatable member being journalled on the body and located axially thereon by a shoulder on the body and an oppositely facing shoulder on a handle extending from at the rear of and attached to the body. It is further preferred, that each block has interengagement with at least one shoulder in the slot to prevent axial displacement of the block, and therefore the component on which the block is provided, relatively to the actuator body.

According to yet another preferred feature of the invention, the distal end of the trochar has one or more cutting edges.

In the preferred construction, there are three trochar components arranged to move on radial paths spaced at 120° around the trochar longitudinal axis, and one component terminates at the distal end, short of the other two components, leaving cutting edges on these two components.

Figure 2:
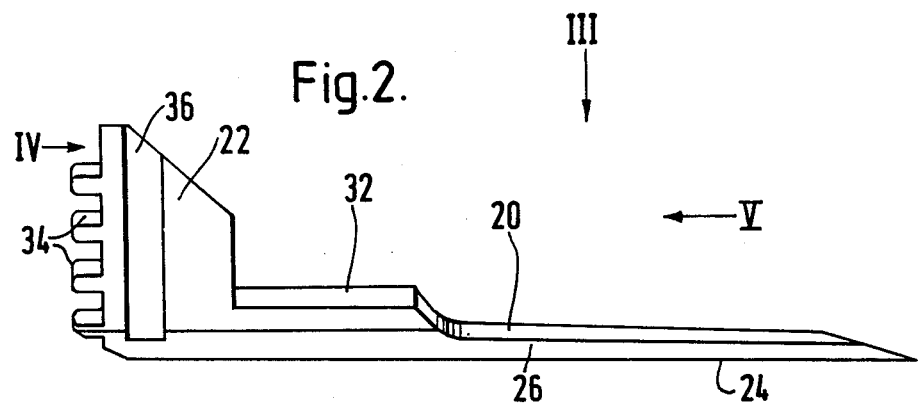
Figure 3:
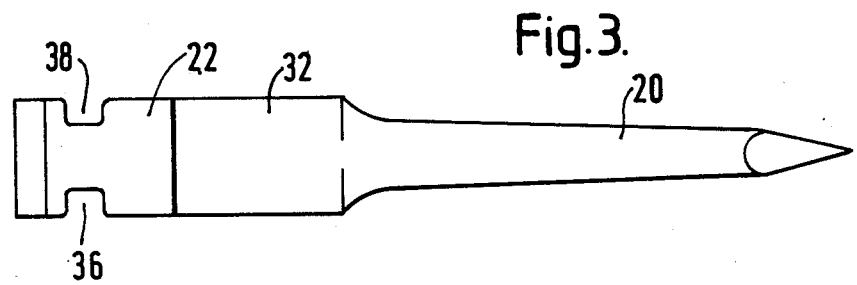
Figure 4:
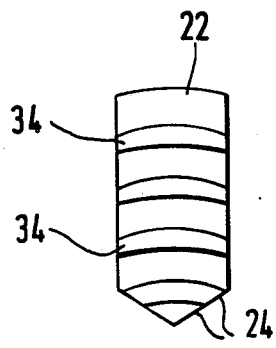
Figure 5:
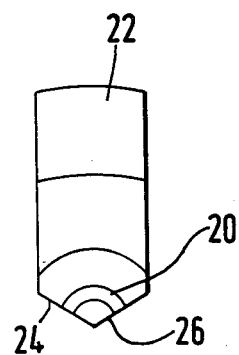
Figure 8:
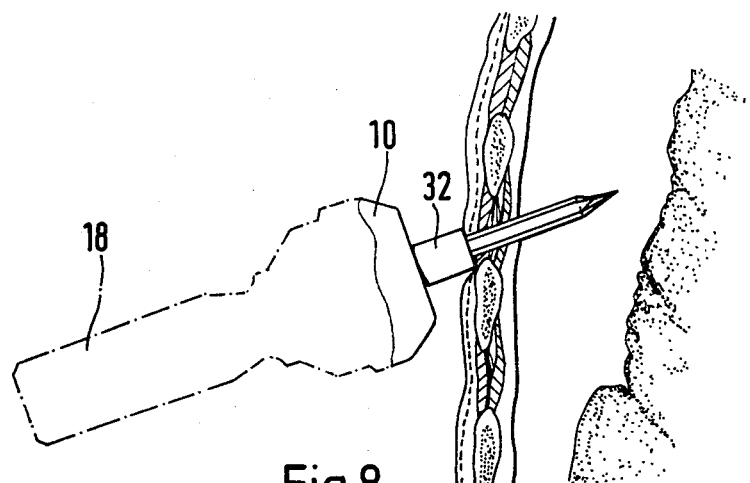
Figure 9:
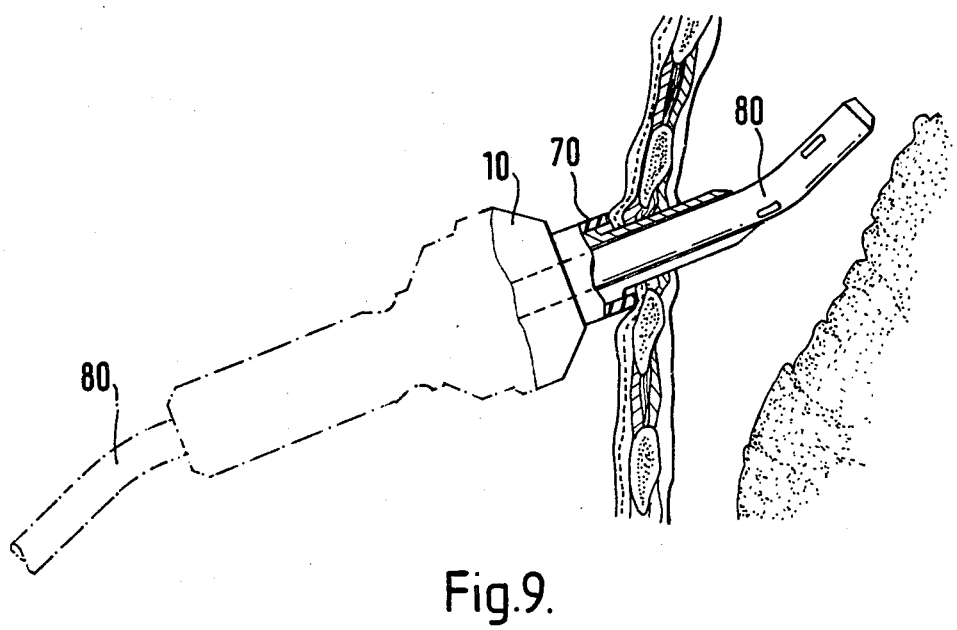

One construction of a surgical appliance in accordance with the invention and a typical method of use, will now be described by way of example only, with reference to the accompanying drawings, in which:

FIG. 1 is a longitudinal cross-section through the appliance in an open condition, FIG. 2 is a side view of a trochar component, FIG. 3 is a plan view of the component shown in FIG. 2, FIG. 4 is an end view of the component looking in the direction of the arrow IV in FIG. 2, FIG. 5 is an end view of the component looking in the direction of the arrow V in FIG. 2, FIG. 6 is a perspective view of the distal end of a trochar, FIG. 7 is a plan view of the complete appliance, FIG. 8 is a view showing the insertion of the trochar through the thoracic wall of a patient, and FIG. 9 is a view similar to FIG. 8, but showing the trochar components opened and a chest drain tube inserted.

The appliance shown in the drawings is intended for use in introducing items such as drain tubes, through the skin tissue of a patient. Perhaps the most common application of an appliance of this nature is as a thoracic drain introducer, in those instances where an intercostal catheter (drain tube) has to be introduced into the thoracic cavity, for example to enable a collapsed or partially collapsed lung to be re-expanded by removing trapped intra-thoracic air or fluid. As will appear hereinafter however, the appliance is not limited to use in thoracic invasion procedures.

The appliance has a body 10, a set of three trochar components 12, 14 and 16, all of which are made of stainless steel or other inert or non-corroding metal, and a handle 18. The whole apparatus is small enough to be gripped by the handle 18 in the hand of the person (usually a hospital house doctor) who is using the appliance. Each of the three trochar components comprises a stem 20 extending cantilever fashion from a block 22 at what will be regarded as the rear end. The block 22 is generally rectangular as seen from the end, but its inside edge 24 is wedge shaped and subtends an angle of approximately 120°. Thus, when all three trochar components are placed together, the wedge shaped inner ends engage with each other and subtend a full circle. The inside edges 26 of the stem 20 are also wedge shaped in continuation of the shape of the inside of the block 22, so that the three stems 20 can also be brought into contact with each other. The outer surfaces of the stems 20 are rounded in cross-section, but taper towards the distal end, so that when the components are closed onto each other (as shown in FIG. 7) they form a single needle-like trochar. The front ends of the components 12, 14 and 16 are pointed, but also chamfered as shown in FIG. 6, and the component 12 does not extend to the point of the other two components 14 and 16. As a result, two relatively sharp edges 28 and 30 appear on the components 14 and 16 at the front end of the trochar. These edges are deliberately made as cutting edges. Each stem also has a thickened portion 32 near to its proximal end, for strengthening it against bending loads, and providing a location for use when the trochar is being inserted.

The trochar constituted by the three components 12, 14 and 16 differs from known thoracic drain trochars mainly in the division into three components, although some of the detail design features are different from the conventional trochar.

The body 10 of the appliance is generally cylindrical, with a sleeve portion 42 and a collar portion 44 at the front end of the sleeve. Three radial slots 40 are formed in the front of the collar 44 at 120° spacings, and one of the blocks 22 is received in each of these slots. Each block 22 is a radial sliding fit in its slot. A vertical notch 36, 38 is formed in each flank of the block 22, and an internal rib 46 projects from each flank of the slot 40 to engage in the corresponding notch 36 and 38. This arrangement prevents axial motion of the block 22 relatively to the body 10, and the blocks can only be moved radially.

On its rear face, each block 22 is formed with a series of parallel teeth 34, each of which extends across the width of the block and has a slightly concave underside and a convex top side. An actuator nut 50 is rotatably mounted on the sleeve 42, and at its front end is formed with a spiral rib 52 and groove 54, the teeth 34 of each block 22 engaging in successive convolutions of the groove 54. The arrangement of the blocks 22 and the actuator nut 50 is similar to that of a scroll type engineers chuck. When the nut 50 is rotated, the blocks 22 are moved inwardly or outwardly depending upon the sense of rotation and the direction of the spiral, due to the action of the spiral rib 52, on the teeth 34. Consequently, the trochar components 12, 14 and 16 are also moved radially inwards or outwards, but it is to be noted that at all times, these components remain parallel with each other—see FIG. 1, which shows the components in the fully opened condition. To facilitate manual rotation of the nut 50, a series of notches 51 is formed in its periphery. Alternatively, there could be protruding finger grips provided on the nut 50 for the same purpose.

A relatively long metal sleeve 56 has its front end screwed into a bore 58 within the body 10, and near to its rear end, this sleeve has an integral collar 60, with an "O" ring seal 62 located in an internal annular groove 64 in the collar portion of the sleeve. The handle 18 is made of metal or plastics and is formed externally for easy gripping. This handle is located on the sleeve 56 and in the assembled appliance is held axially between the collar 60 (which engages in an annular recess 68 in the rear end of the handle) and the rear end of the body 10.

To assemble the appliance, the blocks 22 are engaged in the slots 40; the nut 50 is threaded onto the sleeve portion 42 of the body and engaged with the teeth 34 of the blocks 22, the handle 66 is threaded over the sleeve 56 and the latter is then screwed into the body 10. The handle is then located axially and so is the nut 50. The trochar components can move radially as previously described, but cannot move axially.

A datum marking (not shown) may be made on the collar portion 44 of the body 10, adjacent to the actuator nut 50 (i.e. on a part of the collar 44 not interrupted by one of the slots 40) and a series of spaced indicator markings for co-operating with the datum marking formed on the periphery of the actuator nut 50. Since rotation of the actuator nut relatively to the body produces radial opening of the trochar components, the markings on the nut can be made to correspond with the opening of the trochar components to positions which will allow standard sizes of drain tube to be passed through the space between the opened trochar components.

A short rubber sleeve 70 is provided, and the bore of the sleeve is such that with the components 12, 14 and 16 opened to a condition such that the central space between them will accept a drain tube of a standard size, the sleeve is gripped tightly on the inside and distended by the thickened portions of the components 12, 14 and 16. This sleeve 70 is however completely removable and will not always be used in practice.

Finally, a removable rubber or plastics cap 72 is provided to protect the pointed end of the trochar when the appliance is not in use.

The proposed method of thoracic drain insertion using the surgical appliance just described is illustrated in FIGS. 8 and 9.

Prior to insertion of the drain, the site of insertion is cleaned under sterile conditions and local anaesthetic is injected into the intercostal space. The appliance is adjusted to close the components 12, 14 and 16 onto each other, and then the trochar is pushed through the skin and intercostal muscles into the thoracic cavity (see FIG. 8). This insertion is facilitated by the point of the trochar being acutely sharpened and the diameter of the trochar in the closed condition being small in comparison to the currently available trochars used for thoracic drain insertion. In addition the cutting edges 28 and 30 cut through any obstacle encountered during insertion. The trochar is prevented from being inserted beyond the desirable length by engagement of the enlarged rear portions of the components 12, 14 and 16 with the skin. The components of the trochar are then separated radially by the operator rotating the nut 50 in an anti-clockwise direction. In separating the components 12, 14 and 16 of the trochar, the skin and intercostal muscles are stretched creating a channel into the intercostal space. This channel must be large enough to accept the drain tube, and the components 12, 14 and 16 are in fact opened until it is possible to slide the tube through the space between them. The bore of the sleeve 56 is large enough to allow the largest size of drain tube to pass through it. A thoracic drain tube 80 (see FIGS. 1 and 9) may then be introduced through the open centre of the appliance and through the channel formed through the skin into the thoracic cavity (see FIG. 9). The appliance itself is then withdrawn around the drain tube, leaving the drain tube alone in situ. The skin and intercostal muscles which have been stretched will then contract, firmly gripping the thoracic drain. The exposed part of the drain may then be further secured to the chest wall with adhesive tape, or other known means, and connected to the underwater arm of an underwater seal drain.

When the drain tube is removed, the tissues of the thoracic wall will further contract, sealing the channel created through the skin and muscles and leaving only a small puncture hole in the skin, not requiring closure with a purse string suture.

In some instances, it is regarded as essential to exclude air from the site of the incision, during insertion of the trochar and thoracic drain. If this is required, then the rubber sleeve 70 is fitted around the thickened proximal end portions of the trochar components 12, 14 and 16, when the trochar is in the closed position. When the trochar is forced through the incision in the thoracic wall, the end of the sleeve 70 engages with the skin, and in that case, it is the sleeve 70 which limits the extent of penetration of the trochar into the cavity (see FIG. 9). As the trochar components are expanded, they grip on the inside of the sleeve 70 and distend it somewhat outwardly, but nevertheless, the sleeve remains compressed between the body 10 of the appliance and the skin of the patient. This excludes the atmosphere from immediately around the site of the intrusion. The "O" ring seal 62 itself seals on the drain tube 80, when the latter is inserted, and hence, prevents air travelling through the open centre of the appliance to the site of the trochar entry into the thoracic cavity. Thus, the two seals 62 and 70 combine to prevent the access of air to the site where the drain tube is inserted, until after the insertion has been completed, and the appliance is withdrawn.

Use of the appliance as described above affords a number of advantages over the existing methods of thoracic drain insertion, notably:

Dissection through the thoracic wall is not required prior to insertion of the chest drain. The operation will therefore be less traumatic for the patient than the existing procedure; it will lessen the time required for drain insertion, reduce the risk of haemorrhage and infection and avoid the necessity for the insertion of a purse string suture. Furthermore, it will not leave an unsightly scar. On insertion of the chest drain as described above, there is little or no risk of perforating major vessels, nerves, the lung or heart, all of which are recognised complications in the use of the Argyle type trochar.

The appliance as previously described may be reusable after sterilisation, and a single appliance may be used to insert any of the currently available sizes of thoracic drain tube. In contrast, both the Argyle type apparatus and the Tudor-Edwards type apparatus must be made of a size appropriate to the individual size of thoracic drain to be introduced.

When the thoracic drain has been introduced using the appliance, the skin and the intercostal muscles which have been stretched rather than cut, firmly grip the drain, creating an air tight seal which is not only desirable for the optimal performance of the drain, but should reduce the likelihood of drain displacement and of infection or of haemorrhage occuring at the site of insertion.

On removal of the drain, the stretched tissues contract, occluding the site of insertion, thereby preventing air entering the pleural space from outside and re-collapsing the lung. A small puncture hole is left, in contrast to a dissection channel of up to 1 centimeter in diameter when using the currently available equipment. The puncture hole will not usually require closure with a purse string suture.

In the above specific description, reference has been made to the introduction of a thoracic drain. As has been pointed out however, the use of the appliance is not restricted to insertion of thoracic drains, and indeed it can be used to introduce other surgical items besides drain tubes. For instance, once the trochar has penetrated the tissue and intercostal muscles, a guide wire may be introduced through the centre of the appliance, instead of the drain tube. In one method of use, the trochar portion of the appliance may be guided into the renal pelvis for the introduction of a tube, and extraction of a stone. Similarly, the appliance can be used for the insertion of a tube into the kidney pelvis for the extraction of a stone. Use of the appliance in this manner is likely to produce less complications than use of known apparatus for the removal of stones.

Further uses of this appliance in accordance with the invention include:

introduction of drains into collection of pus or fluid in the abdomen, pelvis or under the diaphragm.

introducing tubing into the abdomen for peritoneal dialysis.

introducing laparoscopes for investigation inside the abdomen, and in some cases to treat lesions or take biopsies.

introducing cystoscopes into the bladder suprapubically for viewing and treating bladder tumours, removing stones and the like, rather than introducing the scope through the urethra, which itself often results in damaged to the urethra. Suprapubic catheters may simultaneously be introduced this way.

introducing tubing or instruments into abdominal organs under radiological control.

If the appliance has a blunt ended "trochar" it may be used for the dilation of ducts, vessels or openings.

I claim:

1. A surgical appliance capable of being temporarily placed in a body for assisting in the passage of a tube through a puncture formed in the skin of the body, contraction of the skin around the tube, once the appliance is removed, assisting in holding the tube in place, said surgical appliance comprising: a trochar having a proximal end, a distal end and being divided into a plurality of separate components; at least one tooth on the proximal end of each of said components; a rotary actuator for said plurality of trochar components, said actuator having a central channel therethrough, a spiral formation on said actuator cooperating with said teeth on said trochar components so that rotation of said actuator about the longitudinal axis of said trochar produces parallel radial motion of each of said trochar components having at least one tooth thereon with respect to each other from a closed position in which such components lie substantially parallel and adjacent to each other thereby to form a composite trochar to an open position wherein such components are substantially axially parallel with each other and separated radially to create a trochar central channel through said trochar components, said trochar central channel formed within said trochar components forming a continuation of said first named central channel through said actuator to provide channel means within said appliance through which a tube can be positioned with one end thereof extending into the puncture, and said appliance being capable of being removed from around the tube to leave only the tube in place within the puncture formed in the skin, contraction of the skin adjacent the puncture around the tube upon removal of said appliance assisting in holding the tube in place.

2. A surgical appliance according to claim 1, wherein the trochar formed by said trochar components has a sharp distal end.

3. A surgical appliance according to claim 1 wherein there is a central opening through said actuator which, when said trochar components are opened, is in continuation of the central channel through those components, whereby it is possible to pass a tube through the entire appliance when the trochar components are open.

4. A surgical appliance according to claim 3, wherein there is an annular tube seal adapted to seal between the appliance and a tube passed through it, and an annular front seal adapted to seal between the appliance and the skin of the patient when the appliance is being used, said two seals together providing at least a restriction on the access of air to the site where the trochar penetrates the skin.

5. A surgical appliance according to claim 1 including a body, and a handle attached to said body, said at least one tooth on each said trochar component being provided on a block extending radially from the proximal end of that component, each of said blocks being received in a radial slot in said body, each said block further having interengagement with at least one shoulder in said slot to prevent axial displacement of said block, and therefore the component on which said block is provided, relatively to said body; said body having a shoulder and said handle having a shoulder facing said shoulder on said body; and said rotary actuator being journalled on said body and being located axially thereon by said shoulder on said body and said oppositely facing shoulder on said handle.

6. A surgical appliance according to claim 1 wherein the distal end of said trochar has at least one cutting edge.

7. A surgical appliance according to claim 1, wherein there are three trochar components arranged to move on radial paths spaced at 120° around the trochar longitudinal axis, and one component terminates at the distal end, short of the other two components, leaving cutting edges on those two components.

* * * * *